(12) United States Patent
Bristow

(10) Patent No.: US 10,077,248 B2
(45) Date of Patent: Sep. 18, 2018

(54) FORM OF IMAZAPYR, A PROCESS FOR ITS PREPARATION AND USE THE SAME

(71) Applicant: ROTAM AGROCHEM INTERNATIONAL COMPANY LIMITED, Chai Wan (HK)

(72) Inventor: James Timothy Bristow, Chai Wan (HK)

(73) Assignee: ROTAM AGROCHEM INTERNATIONAL COMPANY LIMITED, Chai Wan (HK)

( * ) Notice: Subject to any disclaimer, the term of this patent is extended or adjusted under 35 U.S.C. 154(b) by 0 days.

(21) Appl. No.: 14/926,726

(22) Filed: Oct. 29, 2015

(65) Prior Publication Data

US 2017/0121301 A1 May 4, 2017

(51) Int. Cl.
*C07D 401/04* (2006.01)
*A01N 25/04* (2006.01)
*A01N 43/50* (2006.01)

(52) U.S. Cl.
CPC .......... *C07D 401/04* (2013.01); *A01N 25/04* (2013.01); *A01N 43/50* (2013.01)

(58) Field of Classification Search
None
See application file for complete search history.

(56) References Cited

U.S. PATENT DOCUMENTS

| | | | |
|---|---|---|---|
| 4,758,667 A | 7/1988 | Szczepanski et al. | |
| 4,798,619 A | 1/1989 | Los | |
| 2003/0144147 A1* | 7/2003 | Herold | A01N 25/02 504/275 |

FOREIGN PATENT DOCUMENTS

CN 102532102 A 7/2012

OTHER PUBLICATIONS

Vippagunta et al., Crystalline solids, Advanced Drug Delivery Reviews (2001), vol. 48, pp. 3-26.*
Remington's Pharmaceutical Sciences (17th Ed. 1985), p. 1585.*
Crystallization—Science and Technology (2012), pp. 183-204.*
Braga et al., Crystal Growth & Design (2014), vol. 14, pp. 1430-1437.*
Camilleri et al., J. Chem. Soc., Chem. Commu. (1989), pp. 1722, 1723.*
International Search Report dated Oct. 31, 2016, PCT/CN2016/098396; 5 pages.

* cited by examiner

*Primary Examiner* — Hasan Syed Ahmed
*Assistant Examiner* — Frank Choi
(74) *Attorney, Agent, or Firm* — Dickinson Wright PLLC

(57) ABSTRACT

The present invention describes the crystalline form of imazapyr of formula (I), the crystal preparation process, the analyses of the crystal through various analytical methods and using the crystal to prepare stable agrochemical formulation. The invention also describes the use of various solvents towards the crystalline form preparation conditions.

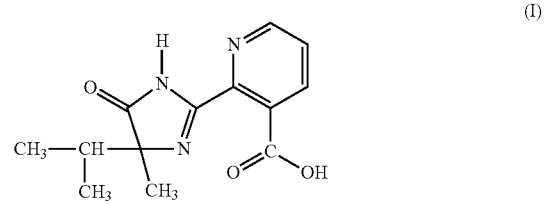

(I)

10 Claims, 4 Drawing Sheets

FORM OF IMAZAPYR, A PROCESS FOR ITS PREPARATION AND USE THE SAME

BACKGROUND

Field

The present disclosure relates to a crystalline form of 2-[(RS)-4-isopropyl-4-methyl-5-oxo-2-imidazolin-2-yl] nicotinic acid (imazapyr), to its preparation processes and to its use in agrochemical preparations.

Description of Related Art

2-[(RS)-4-isopropyl-4-methyl-5-oxo-2-imidazolin-2-yl] nicotinic acid (imazapyr) is a potent herbicide. Imazapyr has molecular formula of $C_{13}H_{15}N_3O_3$. Its chemical structure is:

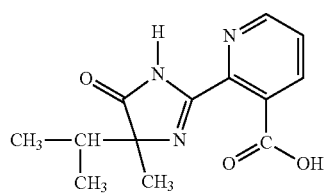

(I)

Imazapyr is a non-selective herbicide used for the control of a broad range of weed including terrestrial annual and perennial grasses and broadleaved herbs, woody species, and riparian and emergent aquatic species. It controls plant growth by preventing the synthesis of branched-chain amino acid. Imazapyr is absorbed quickly through plant tissue and can be taken up by roots. It is translocated in the xylem and phloem to the meristematic tissues, where it inhibits the enzyme acetohydroxy acid synthase (AHAS), also known as acetolactate synthase (ALS). ALS catalyzes the production of three branched-chain aliphatic amino acid, valine, leucine, and isoleucine, required for protein synthesis and cell growth. The rate of plant death usually is slow (several weeks) and is likely related to the amount of stored amino acids available to the plant. Only plants have ALS and produce these three amino acids, and therefore, imazapyr is of low toxicity to animals (including fish and insects). Animals need these three branched chain aliphatic amino acid, but obtain them by eating plants or other animals.

The commercially available imazapyr, which is usually manufactured by the process described in U.S. Pat. No. 4,798,619, is present in amorphous state. It has been found that imazapyr in amorphous state is not suitable for being used in an economical formulation due to the high tendency of aggregation after a long storage time. Therefore, there is a need to provide a novel form of imazapyr with increased storage stability.

SUMMARY

Accordingly an embodiment of the invention provides a novel crystalline form of imazapyr, termed "crystalline modification I", and a process for its preparation as well as its use in agrochemical compositions. The novel crystalline modification I has been found having increased storage stability. Accordingly, an embodiment of the invention also provides compositions for controlling undesirable plant growth, such as weeds, comprising the crystalline modification I of imazapyr on its own, as a mixture with auxiliaries and carriers, and as a mixture with other active compounds. The use of the crystalline modification I of imazapyr in the control of undesired plant growth and a method for the same are also provided by the present invention

BRIEF DESCRIPTION OF DRAWINGS

Various aspects of the invention can be more clearly understood by reference to the drawings, which are described below, and are intended to be illustrative, not limiting, of the invention.

DETAILED DESCRIPTION OF SPECIFIC EMBODIMENTS

Figure 1:
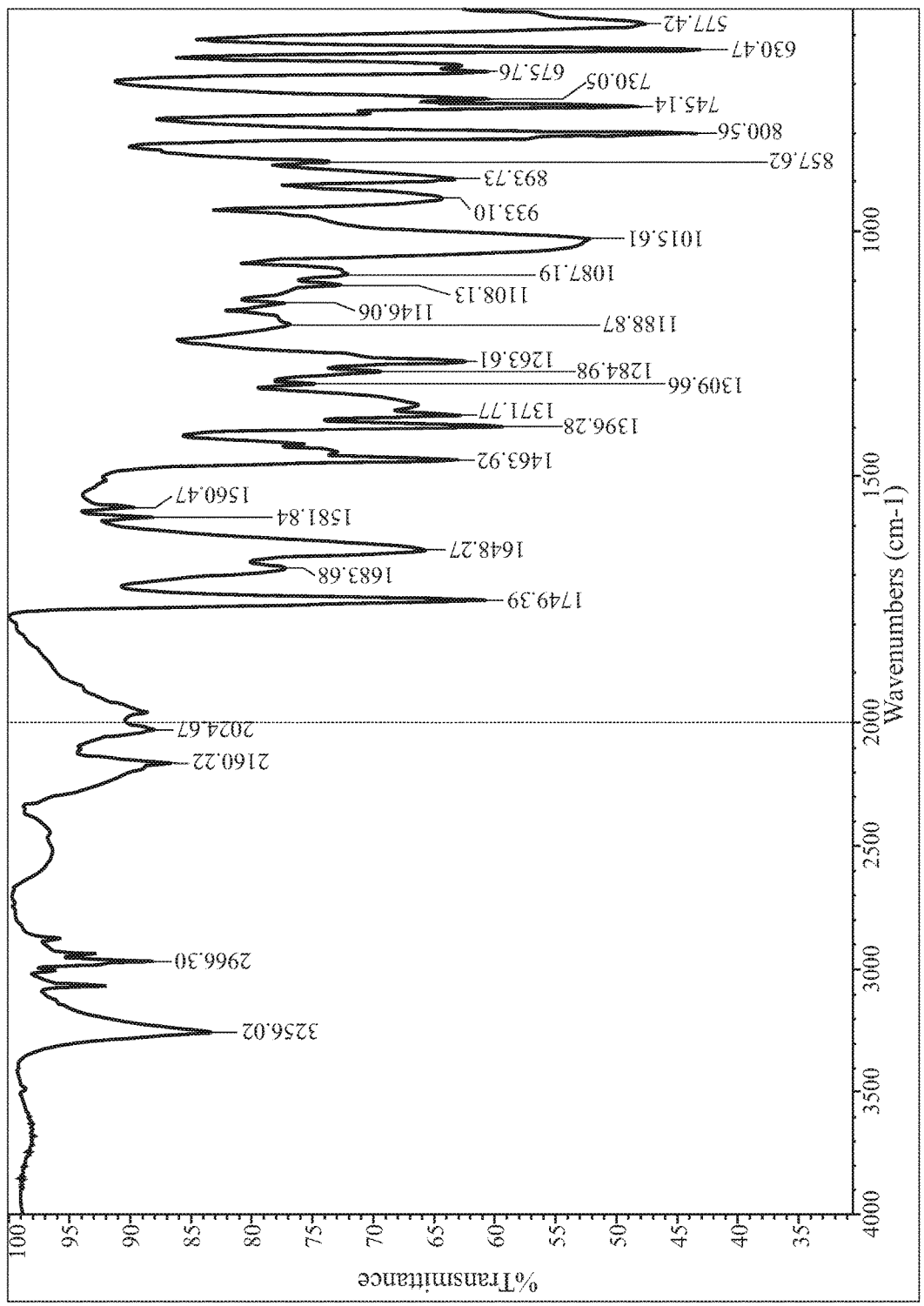
FIG. 1 is a graph showing the results of an infrared (IR) spectrograph of crystalline modification I of imazapyr, according to an embodiment of the invention.

It has been found that the present crystalline modification I of imazapyr has a significant increase in its storage stability, which significantly reduces the aggregation problem encountered in current commercially available formulations. In addition, it is found that the crystalline modification I of imazapyr is easier to be comminuted or ground compared to amorphous imazapyr prepared in accordance with the disclosure of U.S. Pat. No. 4,798,619. This allows the preparation of commercial formulations such as suspension concentrates (SC), oil-based suspension concentrates (OD), water-dispersible granules (WG) and water-soluble granules (SG). Hence, it is possible to prepare any formulations of imazapyr in crystalline modification I, which is disclosed hereinafter.

By virtue of its high stability, the crystalline modification I of imazapyr is highly suitable for preparing compositions for controlling undesirable weeds.

According to a first aspect of the invention a crystalline modification I of imazapyr is provided, exhibiting at least one of the following reflexes as 2θ values in an X-ray powder diffractogram recorded using Cu-Kα radiation at 25° C.:

$$2\theta = 8.09 \pm 0.2 \quad (1)$$

$$2\theta = 9.73 \pm 0.2 \quad (2)$$

$$2\theta = 13.49 \pm 0.2 \quad (3)$$

$$2\theta = 17.17 \pm 0.2 \quad (4)$$

$$2\theta = 19.59 \pm 0.2 \quad (5)$$

$$2\theta = 25.23 \pm 0.2 \quad (6)$$

$$2\theta = 28.38 \pm 0.2 \quad (7)$$

Figure 2:
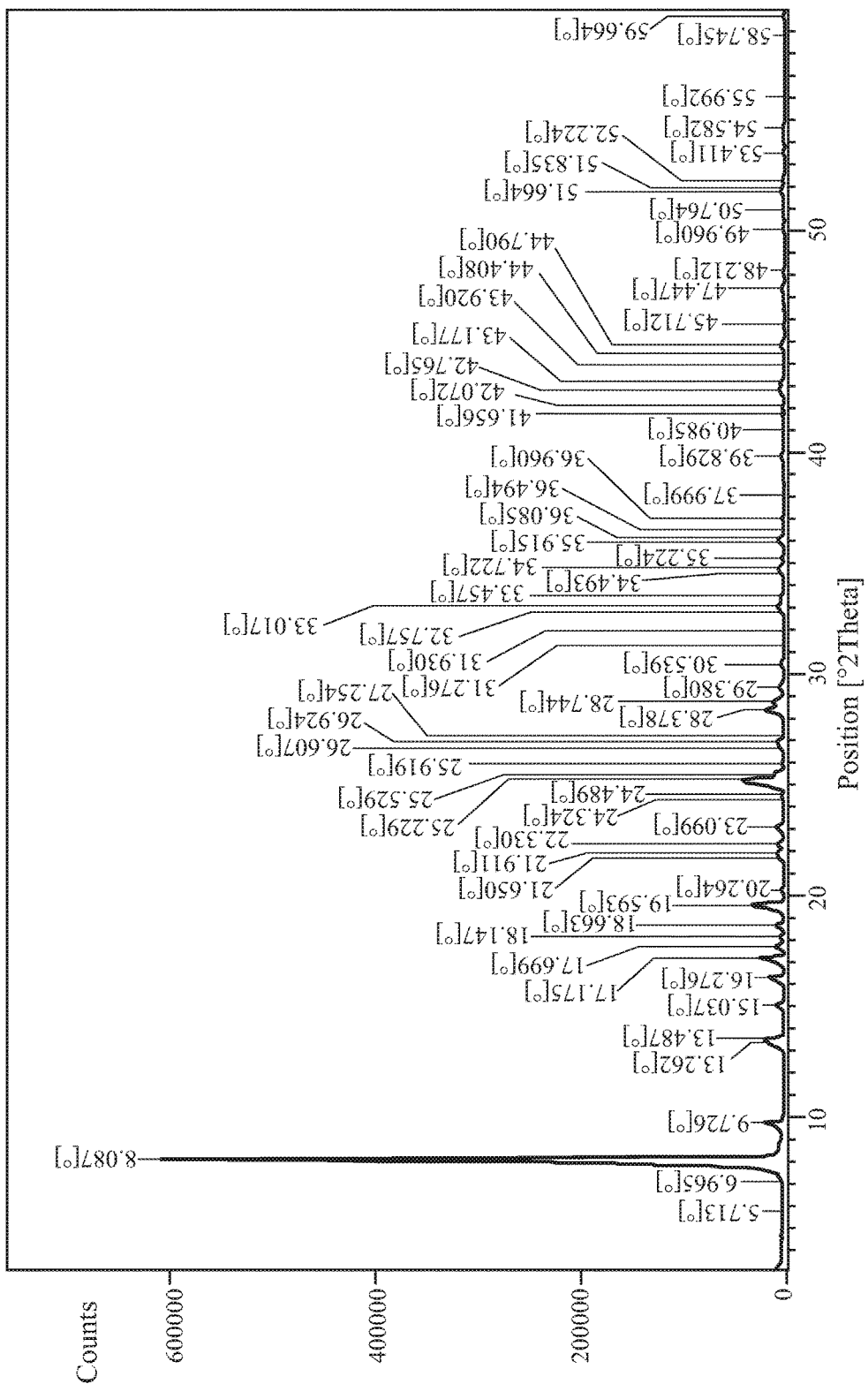
FIG. 2 is a graph showing the results of an X-ray powder diffractogram (XRD) of crystalline modification I of imazapyr, according to an embodiment of the invention.

The crystalline modification I of imazapyr of the present invention is characterized by an X-ray powder diffractogram having at least one of the reflexes indicated above. Preferably, the crystalline modification I is one having at least two of the aforementioned reflexes, more preferably at least three, four, or five of said reflexes. An X-ray powder diffractogram of the crystalline modification I of imazapyr is shown in FIG. 2, which will be described in detail hereinafter.

According to a preferred embodiment the crystalline modification I exhibits at least the reflex from the following:

$$2\theta = 8.09 \pm 0.2 \quad (1)$$

The crystalline modification I of imazapyr according to the present invention may be further characterized by Infrared (IR) spectroscopy. The IR spectrum was measured with the resolution of 4 cm$^{-1}$ and with the number of scans of 16 for the purified sample. The IR spectrum of the crystalline modification I can be identified by its characteristic bands at 3256.02, 2966.30, 2160.22, 2024.67, 1749.39 and 1648.27 cm$^{-1}$ as shown in FIG. 1.

All IR spectra were obtained using the following acquisition parameters:

| | |
|---|---|
| FT-IR spectrometer | Bruker Tensor37 |
| Diamond ATR unit | from Specac |
| Wavelength range | 550-4000 cm$^{-1}$ |
| Resolution | 4 cm$^{-1}$ |
| Number of scans | 16 |

Figure 3:
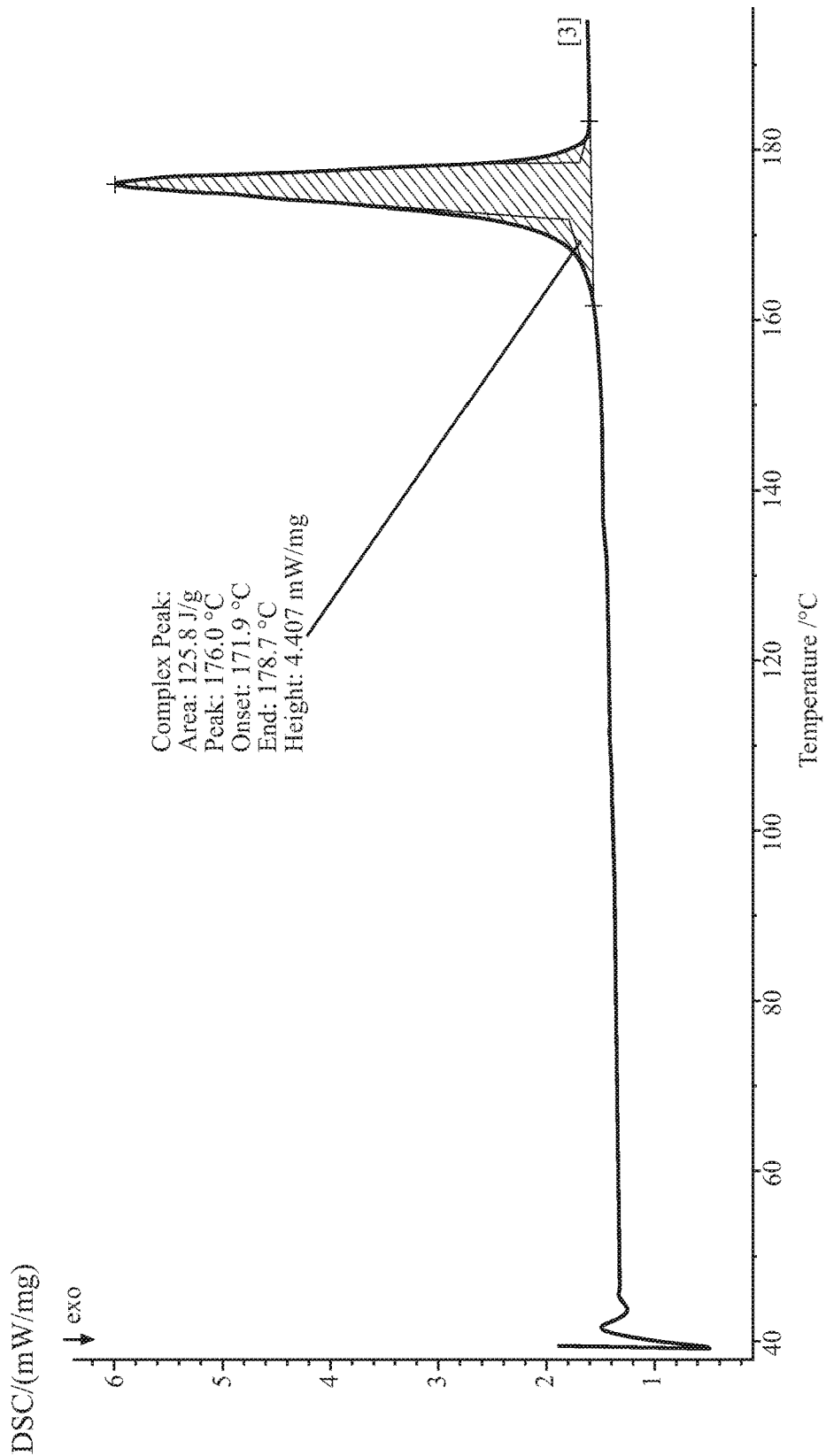
FIG. 3 is a Differential Scanning calorimetry (DSC) thermogram of crystal modification I of imazapyr, according to an embodiment of the invention.

Differential Scanning calorimetry (DSC) analyses were also made for crystallization modification I of imazapyr. The Differential Scanning calorimetry (DSC) spectrum of the crystalline modification I of imazapyr exhibits a peak at 176° C. as shown in FIG. 3.

Methods for preparing amorphous imazapyr are well known in the art. Amorphous imazapyr is manufactured and available on a commercial scale. A particularly suitable method for preparing amorphous imazapyr is described in U.S. Pat. No. 4,798,619.

According to the invention, the crystalline modification I of imazapyr can be obtained by the processes below:

Imazapyr in amorphous state is dissolved and then crystallized from a solvent.

In one aspect, the invention provides a process for preparing a crystalline modification I of imazapyr comprising steps of:

i) preparing a solution of an amorphous imazapyr in a solvent;

ii) effecting crystallization of imazapyr from the solution to obtain a solid precipitate; and iii) isolating the solid precipitate.

Suitable solvents for preparing imazapyr crystalline modification I include halogenated hydrocarbons (for example, trifluoro methyl benzene, chlorobenzene, bromobenzene, dichlorobenzene, chlorotoluene and trichlorobenzene), ethers (for example, ethyl propyl ether, n-butyl ether, anisole, phenetole, cyclohexyl methyl ether, dimethyl ether, diethyl ether, dimethyl glycol, diphenyl ether, dipropyl ether, diisopropyl ether, di-n-butyl ether, diisobutyl ether, diisoamyl ether, ethylene glycol dimethyl ether, isopropyl ethyl ether, methyl tert-butyl ether, tetrahydrofuran, methyltetrahydrofuran, dioxane, dichlorodiethyl ether, methyltetrahydrofuran, polyethers of ethylene oxide and/or propylene oxide), nitrated hydrocarbons (for example, nitromethane, nitroethane, nitropropane, nitrobenzene, chloronitrobenzene and o-nitrotoluene), aliphatic, cycloaliphatic or aromatic hydrocarbons (for example, pentane, n-hexane, n-heptane, n-octane, nonane, ethyl benzene, mesitylene), cymene, petroleum fractions within a boiling range of from 70° C. to 190° C., cyclohexane, methylcyclohexane, petroleum ether, ligroin, octane, benzene, toluene, xylene, esters (for example, malonates, acetic acid n-butyl ester (n-butyl acetate), methyl acetate, ethyl acetate, isobutyl acetate, dimethyl carbonate, diethyl carbonate, dibutyl carbonate and ethylene carbonate), methyl ethyl ketone and aliphatic alcohols (for example, methanol, isopropyl alcohol, ethanol, n-propanol, isopropanol, n-butanol and tert-amyl alcohol).

Preferred solvents are nitrobenzene, toluene, xylene, benzene, chlorobenzene, dichlorobenzene, ethyl benzene, trifluoro methyl benzene, mesitylene, ether, methyl ethyl ketone.

In an embodiment of the invention, it is preferred that the solvent comprises methyl ethyl ketone and/or nitrobenzene.

Hence, according to a preferred embodiment in step (i), amorphous imazapyr is dissolved in a solvent comprising methyl ethyl ketone and/or nitrobenzene.

In step (ii) of the process, imazapyr is crystallized from the solution. Techniques for effecting crystallization of imazapyr from the solution are known to those skilled in the art. For example, in an embodiment where the solution in step (i) is formed at elevated temperatures, crystallization may be effected by cooling the solution to room or ambient temperature or around 0 to 20° C. In one preferred embodiment, crystallization is effected by concentrating the solution formed in step (i) of the process. Alternatively, or in addition thereto, seed crystals, in particular seed crystals of the aforementioned crystalline modification I of imazapyr, may be added to the solution formed in step (i), to facilitate and/or enhance crystallization.

It is preferred that the solid precipitate of imazapyr recovered during the crystallization stage is washed with a solvent for one or more times. Preferably, the solvent employed in the washing stage consists of one or more components of the solvent employed for forming the solution in step (i), as described hereinbefore. Methyl ethyl ketone and nitrobenzene are particularly suitable solvents for washing the recovered solid of imazapyr.

The invention, in an embodiment, also relates to a composition comprising the crystalline modification I of imazapyr. The amount of the crystalline modification I of imazapyr is less than 75% by weight of the composition, preferably less than 50% by weight of the composition, more preferably less than 30% by weight of the composition, still more preferably about 25% by weight of the composition.

The use of imazapyr as a herbicide is well known in the art and is used on a commercial scale. The crystalline modification I of imazapyr is also active in controlling unwanted plant growth, such as weeds. Techniques of formulating and applying imazapyr are known in the art, for example as disclosed in the prior art documents discussed hereinbefore. Imazapyr in the crystalline modification I of the invention may be formulated and applied in an analogous manner.

Accordingly, in a further aspect, the present invention provides a herbicidal composition comprising imazapyr in the crystalline modification I as defined hereinbefore.

Accordingly, the invention furthermore provides processes for preparing compositions for controlling unwanted plant growth using the crystalline modification I of imazapyr.

The crystalline modification I of imazapyr can be converted in a known manner to the customary formulations, such as suspension concentrates (SC), oil-based suspension concentrates (OD), water-soluble granules (SG), dispersible concentrates (DC), emulsifiable concentrates (EC), emulsion seed dressings, suspension seed dressings, granules (GR), microgranules (MG), suspoemulsions (SE) and water-dispersible granules (WG) using suitable auxiliaries, carriers and solvents.

In this context, the crystalline modification I of imazapyr may be present in a concentration of from about 0.1 to about 75% by weight of the total mixture, i.e., in amounts sufficient to achieve the required dosage. The formulations are prepared, for example, by extending the crystalline modification I of imazapyr with water, solvents and carriers, using, if appropriate, emulsifiers and/or dispersants, and/or other auxiliaries.

These formulations are prepared in a known manner by mixing the crystalline modification I of imazapyr with customary additives, for example, liquid diluents, solid diluents, wetting agents, dispersants, thickening agent, antifreeze agents, biocide and any necessary adjuvants and other formulation ingredients.

Liquid diluents include, but are not limited to, water, N,N-dimethylamine, dimethyl sulfoxide, N-alkylpyrrolidone, ethylene glycol, polypropylene glycol, propylene carbonate, dibasic esters, paraffines, alkylbenzenes, alkyl naphthalenes, glycerine, triacetine, oils of olive, castor, linseed, sesame, corn, peanut, cotton-seed, soybean, rape-seed and coconut, ketones such as cyclohexanone, 2-heptanone, isophorone and 4-hydroxy-4-methyl-2-pentanone, acetates such as hexyl acetate, heptyl acetate and octyl acetate, and alcohols such methanol, cyclohexanol, decanol, benzyl and tetrahydrofurfuryl alcohol.

Solid diluents can be water-soluble or water-insoluble. Water-soluble solid diluents include, but are not limited to, salts such as alkali metal phosphates (e.g., sodium dihydrogen phosphate), alkaline earth phosphates, sulfates of sodium, potassium, magnesium and zinc, sodium and potassium chloride, sodium acetate, sodium carbonate and sodium benzoate, and sugars and sugar derivatives such as sorbitol, lactose, sucrose and mannitol. Examples of water-insoluble solid diluents include, but are not limited to clays, synthetic and diatomaceous silicas, calcium and magnesium silicates, titanium dioxide, aluminum, calcium and zinc oxide.

Wetting agents include, but are not limited to, alkyl sulfosuccinates, laureates, alkyl sulfates, phosphate esters, acetylenic diols, ethoxy fluornated alcohols, ethoxylated silicones, alkyl phenol ethyoxylates, benzene sulfonates, alkyl-substituted benzene sulfonates, alkyl a-olefin sulfonates, naphthalene sulfonates, alkyl-substituted naphthalene sulfonates, condensates of naphthalene sulfonates and alkyl-substituted naphthalene sulfonates with formaldehyde, and alcohol ethoxylates. Alkyl naphthalene sulphonates, sodium salts are particularly useful for the composition of the invention.

Dispersants include, but are not limited to, sodium, calcium and ammonium salts of ligninsulfonates (optionally polyethoxylated); sodium and ammonium salts of maleic anhydride copolymers; sodium salts of condensed phenolsulfonic acid; and naphthalene sulfonate-formaldehyde condensates. Of note are compositions comprising up to 10% by weight of dispersant. Ligninsulfonates such as sodium ligninsulfonates are particularly useful for the composition of the invention. Naphthalene sulfonate-formaldehyde condensates such as naphthalenesulfonic acid, polymers with formaldehyde, and sodium salts are particularly useful for the composition of the invention.

Thickening agents include, but are not limited to, guar gum, pectin, casein, carrageenan, xanthan gum, alginates, methylcellulose, hydroxyethylcellulose, hydroxypropylcellulose, and carboxymethylcellulose. Synthetic thickeners include derivatives of the former categories, and also polyvinyl alcohols, polyacrylamides, polyvinylpyrrolidones, various polyethers, their copolymers as well as polyacrylic acids and their salts. Alkylpolyvinylpyrrolidones are particularly useful for the composition of the invention Suitable antifreeze agents are liquid polyols, for example ethylene glycol, propylene glycol or glycerol. The amount of antifreeze agents is generally from about 1% to about 20% by weight, in particular from about 5 to about 10% by weight, based on the total weight of the composition.

Biocides may also be added to the composition according to the invention. Suitable Biocides are those based on isothiazolones, for example Proxel® from ICI or Acticide® RS from Thor Chemie or Kathon® MK from Rohm & Haas. The amount of biocides is typically from 0.05% to 0.5% by weight, based on the total weight of composition.

Other formulation ingredients can also be used in the present invention, such as dyes, defoamers, drying agents, and the like. These ingredients are known to one skilled in the art.

The crystalline modification I of imazapyr according to an embodiment of the invention can be present in its commercially available formulations and in its use forms, prepared from these formulations, and as a mixture with other active compounds (such as insecticides, attractants, sterilizing agents, bactericides, acaricides, nematicides, fungicides, growth-regulating substances, herbicides, safeners, fertilizers and semiochemicals) or with agents for improving plant properties.

When used as herbicide, the crystalline modification I of imazapyr according to an embodiment of the invention can furthermore be present in formulations and its use forms, prepared from these formulations, and as a mixture with inhibitors which reduce degradation of the active compounds after their use in the environment of the plant, on the surface of plant parts or in plant tissues.

All plants and plant parts can be treated in accordance with an embodiment of the invention. In the present context, plants are to be understood as meaning all plants and plant populations such as desired and undesired wild plants or crop plants (including naturally occurring crop plants). Crop plants can be plants which can be obtained by conventional breeding and optimization methods, by biotechnological and genetic engineering methods, or by combinations of these methods, including the transgenic plants and the plant cultivars which can or cannot be protected by plant breeders' rights. Plant parts are to be understood as meaning all parts and organs of plants above and below the ground, such as shoot, leaves, needles, stalks, stems, flowers, fruit bodies, fruits, seeds, roots, tubers and rhizomes. Harvested materials, and vegetative and generative propagation materials, for example, cutting, tubers, meristem tissue, rhizomes, offsets, seeds, single and multiple plant cells and any other plant tissues, are also included.

As used herein, the term "about," when used in connection with a numerical amount or range, means somewhat more or somewhat less than the stated numerical amount or range, to a deviation of ±10% of the stated numerical amount or endpoint of the range.

"Surrounding," as used herein, refers to the place on which the plants are growing, the place on which the plant propagation materials of the plants are sown or the place on which the plant propagation materials of the plants will be sown.

Treatment according to the invention of the plants and plant parts with the compositions or formulations of embodiments of the invention is carried out directly or by allowing the compositions or formulations to act on their surroundings, habitat or storage space by the customary treatment methods. Examples of these customary treatment methods include dipping, spraying, vaporizing, fogging, broadcasting, painting on in the case of propagation material, and applying one or more coats particularly in the case of seed.

The benefits of the invention are seen most when the herbicidal composition is applied to kill weeds in growing crops of useful plants: such as cereals including wheat, barley, durum, triticale, oat, rye, maize and rice, amenity, grassland, cotton, potatoes, sugar beets, plantation crops (such as bananas, fruit trees, rubber trees, tree nurseries), vines, asparagus, bushberries (such as blueberries), caneberries, cranberries, flax, grain sorghum, okra, peppermint, rhubarb, spearmint and sugarcane. In this invention, cereal is more concerned.

All percentages are given in weight % unless otherwise indicated.

Embodiments of the invention will now be described by way of the following examples which are provided for illustrative purposes only, and not intended to limit the scope of the disclosure.

EXAMPLES

Example 1: Preparation of Amorphous Imazapyr in Accordance with the Disclosure of U.S. Pat. No. 4,798,619, Example 5 and 9

Preparation of methyl 2-(4-isopropyl-4-methyl-5-oxo-2-imidazolin-2-yl)nicotinate To 20 ml dry methanol in which 10 mg sodium hydride had reacted was added 2.0 g of a mixture of the imidazopyrrolopyridines. After stirring for 16 hours, 0.03 g glacial acetic acid was added (to neutralize the base), the solution concentrated in vacuo and the residue chromatographed on silica gel in ether. The faster moving material, the desired ester, was obtained in several fractions, combined, concentrated and crystallized from acetonitrile to give the imidazolinyl nicotinate.

Preparation of Imazapyr

To 22.63 g methyl 2-(4-isopropyl-4-methyl-5-oxo-2-imidazolin-2-yl)nicotinate in 100 ml water was added a solution containing 3.29 g sodium hydroxide in 25 ml water and the mixture was heated under reflux with stirring for 1.5 hours. After standing at room temperature overnight, 6.8 ml concentrated hydrochloric acid was added causing a heavy precipitate to form. This was removed by filtration, washed with 20 ml water, followed by 30 ml ether and dried to give 19.27 g acid. This material was dissolved in 350 ml methylene chloride, filtered (to remove a small amount of the isomeric 2-acid) and concentrated to give 17.91 g of pure acid. The analytically pure sample was prepared by recrystallization of the material from acetone-hexane.

Figure 4:
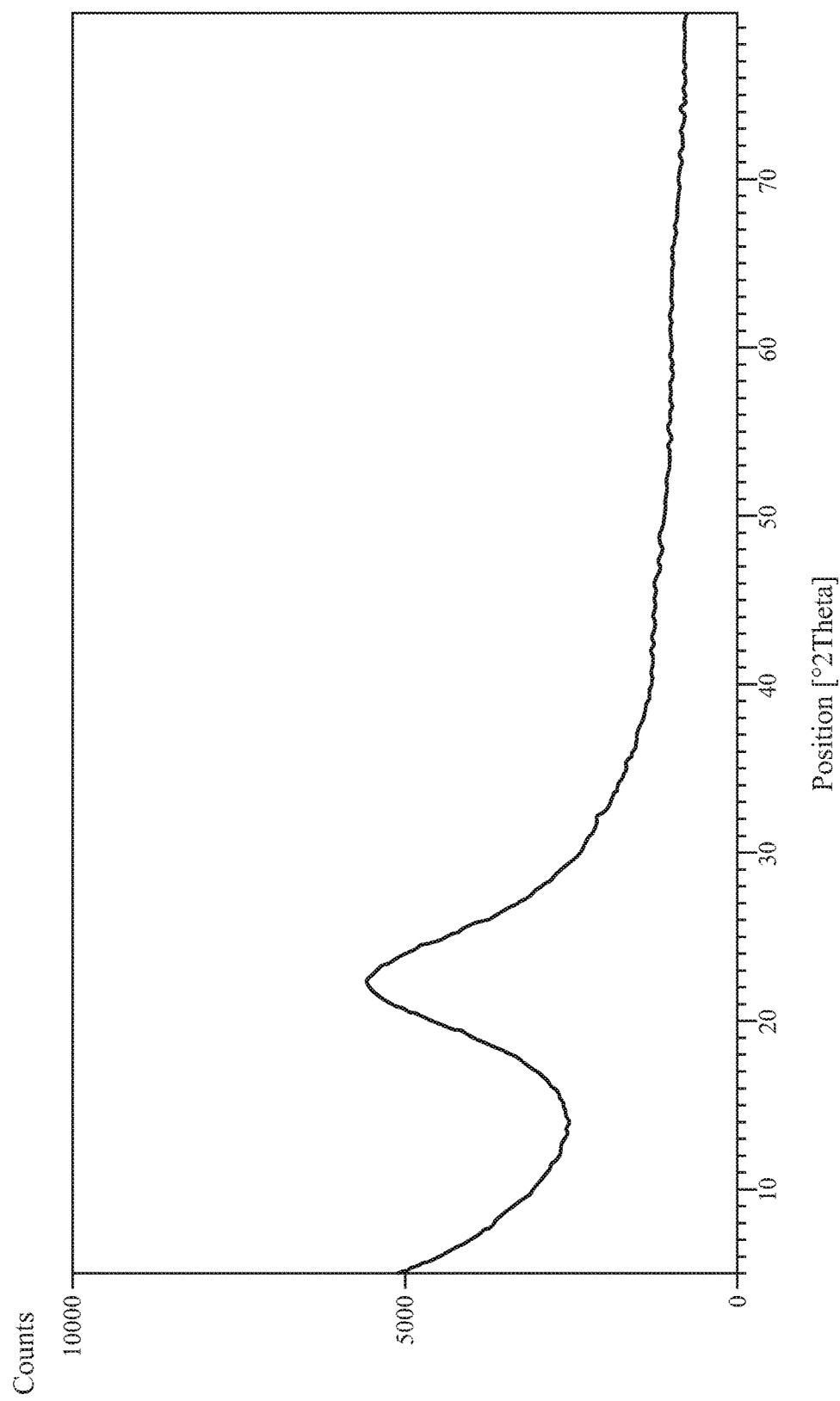
FIG. 4 is a graph showing the results of an X-ray powder diffractogram of amorphous imazapyr.

As shown in FIG. 4, the X-ray powder diffraction pattern of the resulting imazapyr product has no significant signals, which indicates the imazapyr product prepared in accordance with the disclosure of U.S. Pat. No. 4,798,619 is amorphous.

Example 2: Preparation of the Crystalline Modification I of Imazapyr

Crystallization from Methyl Ethyl Ketone 10 g of imazapyr sample prepared in Example 1 was taken in a 3 neck round bottom flask along with 50 mL of methyl ethyl ketone and the resulting slurry was heated to 65° C. to get a homogeneous solution. The insoluble particles, if any, were filtered and the solution was slowly cooled to ambient temperature. Fine crystals were formed during the cooling and the mixture was stirred at ambient temperature for 2 h. Then, the slurry was filtered and washed with 3 mL of methyl ethyl ketone. The filtered crystals were dried under vacuum at 40° C. in order to remove the methyl ethyl ketone traces from the crystalline product. The crystal product thus obtained was having a purity of >98% and the yield was found to be not less than 90%.

The crystals were characterized as being the crystalline modification I of imazapyr using IR spectrometry, X-ray powder diffraction and DSC, respectively.

The IR spectrum of the crystalline modification I of imazapyr is set out in FIG. 1. The IR spectrum exhibits characteristic peaks at 3256.02, 2966.30, 2160.22, 2024.67, 1749.39 and 1648.27 $cm^{-1}$.

The crystalline modification I of imazapyr has the X-ray powder diffractogram shown in FIG. 2 with the reflexes listed in Table 1 below.

TABLE 1

| Crystalline Modification I | |
|---|---|
| 2θ (°) | d (Å) |
| 8.09 ± 0.2 | 10.93 ± 0.05 |
| 9.73 ± 0.2 | 9.09 ± 0.05 |
| 13.49 ± 0.2 | 6.57 ± 0.05 |
| 17.17 ± 0.2 | 5.16 ± 0.05 |
| 19.59 ± 0.2 | 4.53 ± 0.05 |
| 25.23 ± 0.2 | 3.53 ± 0.05 |
| 28.38 ± 0.2 | 3.14 ± 0.05 |

The DSC shows an endothermic peak at 176° C. as shown in FIG. 3.

Example 3: Preparation of the Crystalline Modification I of Imazapyr

Crystallization from Nitrobenzene 5 g of imazapyr sample prepared in Example 1 was taken in a 3 neck round bottom flask along with 30 mL of nitrobenzene and the resulting slurry was heated to 83° C. to get a homogeneous solution. The insoluble particles, if any, were filtered and the solution was slowly cooled to ambient temperature. Fine crystals were formed during the cooling and the mixture was stirred at ambient temperature for 2 h. Then, the slurry was filtered, washed with 3 mL of nitrobenzene. The filtered crystals were dried under vacuum at 45° C. in order to remove the nitrobenzene traces from the crystalline product. The crystal product thus obtained was having a purity of >98% and the yield was found to be not less than 90%.

The crystals were characterized as being the crystalline modification I of imazapyr using IR spectrometry, X-ray powder diffraction and DSC as described in Example 2.

Formulation Examples

Example 4—Preparation of Suspension Concentrate (SC) of Amorphous Imazapyr

All the components list in Table 2 below were mixed uniformly and the resulting mixture was ground with a Dyno-Mill (manufactured by Willy A. Bachofen AG) to obtain a suspension concentrate.

TABLE 2

| Content | Weight % | Function |
|---|---|---|
| Amorphous imazapyr, 98% (prepared in example 1) | 25.51 | Active ingredient |
| Sodium alkyl naphthalene sulfonate | 18.00 | Surfactant |
| Alkylpolyvinylpyrrolidone | 15 | Thickening agent |
| Butylated hydroxytoluene (BHT) | 5 | Antioxidant |
| Propylene glycol | 10 | Antifreeze |
| 1,2-Benzisothiazol-3(2H)-one (Proxel ®) | 1 | biocide |
| Water | 25.49 | Filler |

Example 5—Preparation of Suspension Concentrate (SC) of Imazapyr Crystalline Modification I All the components list in Table 3 below were mixed uniformly and the resulting mixture was ground with a Dyno-Mill (manufactured by Willy A. Bachofen AG) to obtain a suspension concentrate.

TABLE 3

| Content | Weight % | Function |
|---|---|---|
| Imazapyr, crystalline modification I, 98% (prepared in example 2) | 25.51 | Active ingredient |
| Sodium alkyl naphthalene sulfonate | 18.00 | Surfactant |
| Alkylpolyvinylpyrrolidone | 15 | Thickening agent |
| Butylated hydroxytoluene (BHT) | 5 | Antioxidant |
| Propylene glycol | 10 | Antifreeze |
| 1,2-Benzisothiazol-3(2H)-one (Proxel ®) | 1 | biocide |
| Water | 25.49 | Filler |

Example 6: Comparison of the Storage Stability

Samples prepared in Examples 4, and 5 were stored at 54° C. for 1 month, 3 months and 6 months. The procedures are followed according to CIPAC MT 46.3. The concentration of imazapyr was tested at the end of each storage time by high pressure liquid chromatography (HPLC). The aggregation was measured by observation. The original concentration of imazapyr in each formulation was 25%. The results are listed in Table 4.

TABLE 4

| | 1 month | | 3 month | | 6 month | |
|---|---|---|---|---|---|---|
| Sample | Concentration of imazapyr (%) | Aggregation | Concentration of imazapyr (%) | Aggregation | Concentration of imazapyr (%) | Aggregation |
| Example 4 | 20 | + | 12 | +++ | 10 | +++++ |
| Example 5 | 25 | − | 25 | − | 24 | − |

Remark:
"+" means small amount of aggregation.
"+++++" means a lot of aggregation.
"−" means no aggregation.

The invention claimed is:

1. A crystalline modification I of imazapyr, obtained by (i) mixing imazapyr with a polar solvent to create a slurry, wherein the polar solvent is methyl ethyl ketone or nitrobenzene or a mixture thereof, (ii) heating the slurry to prepare a homogeneous solution, (iii) filtering the homogeneous solution to remove any insoluble particles, (iv) cooling the solution to form crystals, (v) mixing the cooled crystalline solution, (vi) filtering the crystalline solution to obtain filtered crystals, (vii) washing the filtered crystals with the polar solvent, and (viii) drying the washed crystals under vacuum,
wherein the obtained crystalline modification I of imazapyr exhibiting each of the following reflexes in an X-ray powder diffractogram recorded using Cu-Kα radiation at 25° C.:

$$2\theta = 8.09 \pm 0.2 \quad (1)$$

$$2\theta = 9.73 \pm 0.2 \quad (2)$$

$$2\theta = 13.49 \pm 0.2 \quad (3)$$

$$2\theta = 17.17 \pm 0.2 \quad (4)$$

$$2\theta = 19.59 \pm 0.2 \quad (5)$$

$$2\theta = 25.23 \pm 0.2 \quad (6)$$

$$2\theta = 28.38 \pm 0.2 \quad (7).$$

2. The crystalline modification I of imazapyr according to claim 1, exhibiting IR spectrum with the characteristic bands at 3256.02, 2966.30, 2160.22, 2024.67, 1749.39 and 1648.27 cm$^{-1}$.

3. The crystalline modification I of imazapyr according to claim 1 exhibiting a Differential Scanning calorimeter (DSC) thermogram having a single predominant endotherm at 176° C.

4. A composition comprising the crystalline modification I of imazapyr according to claim 1 and at least one auxiliary.

5. The composition according to claim 4, in form of a suspension concentrate (SC), an oil-based suspension concentrate (OD), water-soluble granules (SG), a dispersible concentrate (DC), an emulsifiable concentrate (EC), an emulsion seed dressing, a suspension seed dressing, granules (GR), microgranules (MG), a suspoemulsion (SE), or water-dispersible granules (WG).

6. The composition according to claim 5, in form of a suspension concentrate (SC).

7. The composition according to claim 4, wherein the auxiliary is selected from one or more of a solvent, a diluent, a wetting agent, a dispersant, a thickener, an antifreeze agent, and a biocide.

8. The composition according to claim 4, which comprises crystalline modification I of imazapyr in an amount of less than 75% by weight.

9. A method of controlling unwanted plant growth, comprising the step of: applying a crystalline modification I of imazapyr to a plant and/or weed, wherein the crystalline modification I of imazpryr obtained by (i) mixing imazapryr with a polar solvent to create a slurry, wherein the polar solvent is methyl ethyl ketone or nitrobenzene or a mixture thereof, (ii) heating the slurry to prepare a homogeneous solution, (iii) filtering the homogeneous solution to remove any insoluble particles, (iv) cooling the solution to form crystals, (v) mixing the cooled crystalline solution, (vi) filtering the crystalline solution to obtain filtered crystals, (vii) washing the filtered crystals with the polar solvent, and (viii) drying the washed crystals under vacuum, and the crystalline modification I of imazapyr exhibiting each of the following reflexes in an X-ray powder diffractogram recorded using Cu-Kα radiation at 25° C.:

$2\theta = 8.09 \pm 0.2$ (1)

$2\theta = 9.73 \pm 0.2$ (2)

$2\theta = 13.49 \pm 0.2$ (3)

$2\theta = 17.17 \pm 0.2$ (4)

$2\theta = 19.59 \pm 0.2$ (5)

$2\theta = 25.23 \pm 0.2$ (6)

$2\theta = 28.38 \pm 0.2$ (7).

10. A method of controlling unwanted plant growth, comprising the step of: applying a composition including a crystalline modification I of imazapyr and at least one auxiliary to a plant and/or weed, wherein the crystalline modification I of imazapryr obtained by (i) mixing imazapryr with a polar solvent to create a slurry, wherein the polar solvent is methyl ethyl ketone or nitrobenzene or a mixture thereof, (ii) heating the slurry to prepare a homogeneous solution, (iii) filtering the homogeneous solution to remove any insoluble particles, (iv) cooling the solution to form crystals, (v) mixing the cooled crystalline solution, (vi) filtering the crystalline solution to obtain filtered crystals, (vii) washing the filtered crystals with the polar solvent, and (viii) drying the washed crystals under vacuum, and the crystalline modification I of imazapyr exhibiting each of the following reflexes in an X-ray powder diffractogram recorded using Cu-Kα radiation at 25° C.:

$2\theta = 8.09 \pm 0.2$ (1)

$2\theta = 9.73 \pm 0.2$ (2)

$2\theta = 13.49 \pm 0.2$ (3)

$2\theta = 17.17 \pm 0.2$ (4)

$2\theta = 19.59 \pm 0.2$ (5)

$2\theta = 25.23 \pm 0.2$ (6)

$2\theta = 28.38 \pm 0.2$ (7).

\* \* \* \* \*